United States Patent [19]

Rüsch

[11] 4,289,128

[45] Sep. 15, 1981

[54] LARYNGEAL TUBE

[75] Inventor: Heinz Rüsch, Waiblingen, Fed. Rep. of Germany

[73] Assignee: Willy Rusch GmbH & Co. KG., Kernen, Fed. Rep. of Germany

[21] Appl. No.: 49,021

[22] Filed: Jun. 15, 1979

[30] Foreign Application Priority Data

Jun. 29, 1978 [DE] Fed. Rep. of Germany ....... 2828447

[51] Int. Cl.³ .......................................... A61M 16/00
[52] U.S. Cl. .......................... 128/207.15; 128/204.25
[58] Field of Search ....................... 128/207.15, 207.14, 128/349 R, 349 B, 349 BV, 200.26, 204.25

[56] References Cited

U.S. PATENT DOCUMENTS

| | | | |
|---|---|---|---|
| 3,314,431 | 4/1967 | Smith, Jr. | 128/200.26 |
| 3,407,817 | 10/1968 | Galleher, Jr. | 128/207.15 |
| 3,503,401 | 3/1970 | Andersen et al. | 128/349 R |
| 3,881,479 | 5/1975 | Carden | 128/207.15 |
| 4,180,076 | 12/1979 | Betancourt | 128/349 B |
| 4,185,639 | 1/1980 | Linder | 128/200.26 |

FOREIGN PATENT DOCUMENTS 2426344 9/1977 Fed. Rep. of Germany .
1447987 9/1976 United Kingdom .

OTHER PUBLICATIONS

Litton, Tracheoplast-Plastik Endotracheal Katheter, Prospekt der Firma Sterimed.

*Primary Examiner*—Henry J. Recla
*Attorney, Agent, or Firm*—William D. Hall; Darle M. Short

[57] ABSTRACT

In a laryngeal tube for use in microsurgery in the region of the larynx, with simultaneous ventilation and anaesthesia, which, at its introduction end, is provided with a tube bearing an inflatable cuff, and which is also provided with an inflation channel terminating in the inside of the cuff, and also a ventilation channel terminating within the lumen of the tube, provision is made for the inflation channel (6) and the ventilation channel (7) to be connected together and stiffened.

21 Claims, 4 Drawing Figures

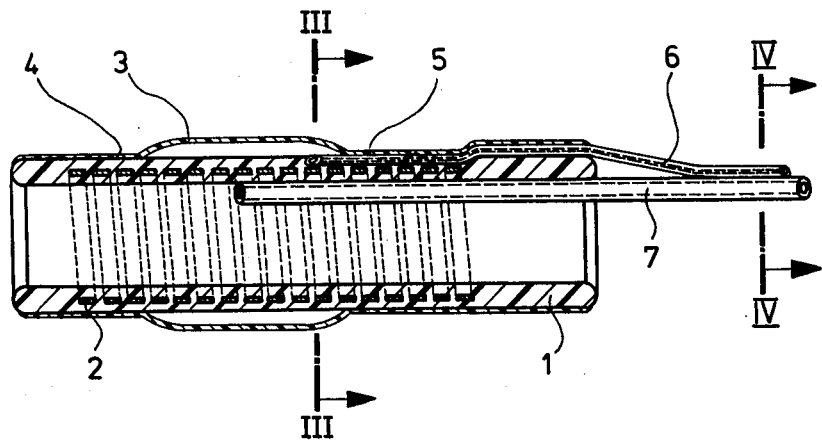
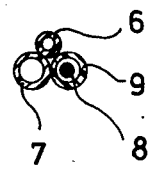
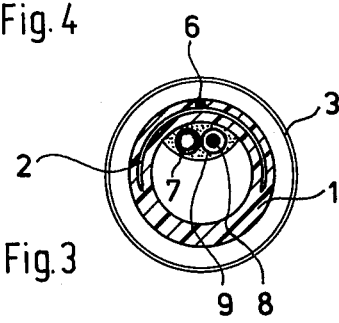
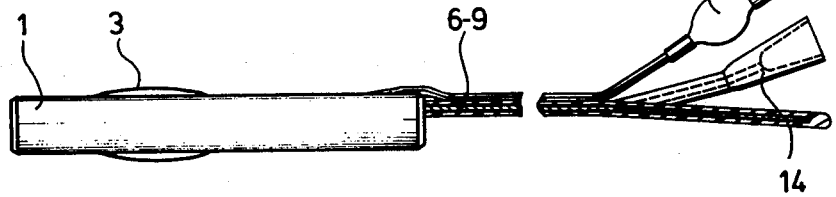

LARYNGEAL TUBE

BACKGROUND OF THE INVENTION

This invention relates to a laryngeal tube for use in microsurgery in the region of the larynx with simultaneous ventilation and anaesthesia, with a tube at the introduction end, the said tube being provided with an inflatable cuff, and incorporating an inflation channel terminating in the inflatable cuff, together with a ventilation channel terminating in the inside lumen of the tube.

Such a tube for use in endolaryngeal microsurgery, is known as the Carden tube. The tube, which is preferentially provided with a stiffening helical spring, which is embedded in the material of the tube, is passed into the trachea of the patient with the aid of a foreign body-removing forceps. Then, the inflatable cuff is inflated with the aid of the inflation channel, with the result that it presses firmly against the inside surface of the trachea. In the introduction end section of the tube, a ventilation channel is located in such a way that it terminates in the lumen of the tube; through this ventilation channel, oxygen and an anaesthetic gas is supplied to the patient by means of a ventilation apparatus. The cuff prevents blood arising at the site of the operation above the tube from getting into the bronchi. However, when an operation is being performed in the region of the larynx, the two channels, which are not immobilized and which, in addition, move in the flow of air, are disturbing. Admittedly, the two channels cannot be dispensed with, since one is needed for ventilation and the other for inflating and deflating the cuff, and also because, on the other hand, the necessary sealing effect between the tube and the trachea could then not be achieved.

SUMMARY OF THE INVENTION

The objective of the present invention is to provide an improved laryngeal tube of the type mentioned initially, which, when surgery is being carried out, hinders and disturbs the surgeon to a smaller degree.

This objective has been realized by this invention by connecting the inflation channel and the ventilation channel together so that, as a result, they are stiffened. Thus, there is only a single tube leading upwards, so that the surgeon can work better and with more despatch. Furthermore, on account of its enhanced stiffness, the single tube (double-tube) moves less. The increased stiffness is a result of the fact that the two channels are glued or welded to each other, so that, by this means, each provides support to the other. In a specially preferred embodiment of the invention, to provide further stiffening, a wire, provided with a protective sheathing is incorporated, with which the two channels are connected. In this embodiment of a laryngeal tube of this invention, the two channels are so well fixed that they virtually do not move, and cannot disturb the surgeon carrying out the operation. The sheathing protects the patient from pressure points, and the stiffness of the wire makes it possible, if necessary, even to pass the tube without the need for a foreign body-removing forceps and to advance it solely by means of the wire. Thus, all disadvantageous properties of the known laryngeal tubes—which are frequently disturbing during operation—have been eliminated.

The wire can be made of an adequately stiff and mouldable plastic material. Preferentially, however, it is made of a flexible metal, such as soft iron, copper, aluminium, stainless steel or suchlike. By this means, the surgeon can give the channels any shape he likes and fix them, so that during the surgical operation, no part of their introduced length has a disturbing influence.

The wire might be embedded in the material of the tube. Preferentially, however, it terminates in the lumen of the tube in the same way as the ventilation channel terminates inside the tube. This has technical advantages for the manufacturing process and, in comparison with an attachment to the outside of the tube, the advantage that the contours of the latter remain round.

Preferentially, the wire and the ventilation channel, running next to each other, are connected together and introduced into the tube, to the inside surface of whose walls they are attached. In a preferred further improvement, the inflation channel, which has a smaller diameter, is located in the wedge-shaped space between the sheathing of the wire and the ventilation channel and connected with them. This improved version has the advantage of a particularly low cross-sectional requirement of the channel and stiffening configuration.

The wire, together with its sheathing, the inflation and the ventilation channel are separated one from the other only in the extreme end section, so that connection possibilities of the ventilation channel to a ventilation unit, in particular an injection ventilation unit, and of the inflation channel to an appropriate syringe is in no way hindered. Also, irrespective of the two channels, the extreme end of the wire can be affixed to a stand, or also to the patient in an expedient manner.

In contrast to the ventilation channel and to the stiffening wire, in preferred embodiments of the invention, the inflation channel is embedded within the tube or is arranged in a gutter in the outer surface of the tube. This has technical advantages for the production process, since the end of the inflation channel opens into the cuff attached to the outside of the tube. In this way, a perforation of the tube for the purpose of leading the inflation channel into the inside space of the cuff is not needed.

The ventilation channel terminates in the end section of the introduction end of the tube, while the wire and/or the inflation channel teminates approximately halfway along the tube. This dimensioning and arrangement is expedient.

It goes without saying that, instead of the sheathed wire, a rod made of plastics having comparable properties, the material of which being uniform or variable over the cross-section, can also be employed. Equally, the arrangement can be such that the two channels are glued together or welded together or otherwise connected and the wedge-shaped space remaining between the two channels filled with an appropriate plastic mass which provides an adequate stiffness. Further details of, and improvements to, the present invention can be seen in the following description of one embodiment represented in the drawing, in conjunction with the claims. In a simplified and schematic form, the following aspects are illustrated:

IN THE DRAWINGS

FIG. 1 A view of a laryngeal tube of the invention,

FIG. 2 A longitudinal section through the introduction end of the tube shown in FIG. 1, the view being enlarged as compared with FIG. 1, FIG. 3 A section along the line III—III of FIG. 2 and FIG. 4 A section along the line IV—IV of FIG. 2.

DETAILED DESCRIPTION OF THE DRAWINGS

The represented laryngeal tube for intratracheal intubation anaesthesia, for use in microsurgical interventions in the region of the larynx, comprises a tube, 1, attached at the introduction end, the said tube being made of soft PVC or rubber or suchlike, and having a diameter matched to the cross-section of the trachea, the said tube comprising a soft-plastic tube-like section with rounded ends, and in which a metal helical spring, 2, is embedded in order to increase its stiffness and, in particular, its resistance to crushing. The coils of the metal helical spring preferentially have a rectangular cross-section. The metal helical spring terminates at a short distance before the introduction end of the tube, 1, and at a larger distance from the opposite end of tube 1. To the outside of tube, 1, displaced somewhat from the middle of the tube in the direction towards the introduction end, a cuff, 3, is attached, the said cuff being made of a thin elastic layer, for example, soft PVC or latex, and having the form of a section of a tube and whose two ends, 4 and 5, are affixed tightly to the outside surface of tube, 1. In the empty state, the cuff, 3, lies virtually flat against the outside surface of the tube, 1, possibly being slightly vaulted, and thus does not hinder the introduction of the tube, 1 into the trachea. On the outside surface of the tube, 1, or sunk into its wall, there is a thin inflation channel, 6, having a very fine lumen, and which passes beneath the end, 5, of the cuff, 3, and which opens into the annular space which is closed to the outside by the cuff, 3.

In approximately the same longitudinal plane as the inflation channel, 6, a ventilation channel, 7, is provided, the said ventilation channel having a larger inside cross-section as compared with the inflation channel, 6, and running along the inside surface of the tube, 1, and opening at a distance from the introduction end of the tube, 1, approximately in the region of the end, 4, of the cuff, 3 (but within the lumen of tube, 1).

The ventilation channel, 7, serves to supply oxygen for respiration and an anaesthetic gas, and also for the expiration of carbon dioxide.

Immediately adjacent to the ventilation channel, 7, a mouldable stiffening wire, 8, made of soft iron, copper, aluminium, stainless steel or other material with similar properties, is arranged, the said wire being provided with a sheathing, 9, made of plastics. The stiffening wire, 8, can be relatively easily moulded, for example, as can a copper or soft iron wire, but is adequately robust to keep the channels, 6 and 7, in a desired position. For this purpose, the ventilation channel, 7 and the sheathing, 9, of the stiffening wire, 8, are connected to each other along their entire length, for example, by gluing or welding. As from the end of the tube, 1, directed outwards, the inflation channel, 6, is also connected to the sheathing, 9, and the ventilation channel, 7, the said ventilation channel, 7, and the stiffening wire, 8, together with the sheathing, 9, being arranged next to each other and lying against each other, and the inflation channel, 6, is located in the wedge-shaped space between the sheathing, 9, and the ventilation channel, 7, and glued therein.

At the extreme end of the inflation channel, 6, which is directed away from the tube, 1, a pilot balloon, 10, is attached, to which, via an intermediate line, 11, a known inflation funnel, 12, provided with a spigot, 13, is connected. Through the inflation funnel, 12, and the intermediate line, 11, an inflating gas can be introduced into the cuff, 3, the state of filling of which being indicated by the pilot balloon, 10.

At the extreme end of the ventilation channel, 7, a connecting funnel, 14, is attached.

When carrying out microsurgical interventions in the region of the larynx, the patient is first premedicated with appropriate means prior to the operation and is given an agent to induce relaxation. After thorough oxygenation, the laryngeal tube is passed, this generally being possible without the necessity to employ a foreign body-removing forceps, since the stiffening wire, 8, possesses adequate firmness. When the tube, 1, has reached its final position in the trachea of the patient, the cuff, 3, is inflated via the inflation channel, 6, the result being that the cuff presses against the inside surface of the trachea, thus forming a seal. To the connection funnel, 14, of the ventilation channel, 7, an injector ventilation device is connected, the said device ventilating the patient with an intermittent positive pressure; the ventilation pressure, and thus the respiratory minute volume, can be set. Furthermore, the respiration rate and the ratio of inspiration to expiration can be varied. In addition, an anaesthetic gas, for example laughing gas (nitrous oxide) is admixed with the respiratory oxygen.

Thanks to the joining of the inflation channel, 6, with the ventilation channel, 7, and the additional provision of the stiffening wire, 8, provided with a sheathing, 9, not only is the placement of the tube, 1, facilitated, but, in addition, the channels are retained in a position in which they do not disturb the surgeon carrying out an operation.

It goes without saying that the invention is not restricted to the embodiment represented here, but that deviations are possible, without exceeding the scope of the invention. In particular, individual characteristics or features of the invention can be used, either alone or combined severally.

I claim:

1. In a laryngeal tube for use during surgery on a patient:
    means for insertion in the larynx including a first tube,
    inflatable cuff means, located around at least a portion of said first tube, for holding the first tube in the larynx when the cuff means is inflated,
    elongated means extending from said first tube to the mouth when the first tube is in the larynx including (a) means for inflating the cuff means comprising a second tube which when in use extends at least part of the distance from the mouth of the patient to said cuff means, and (b) ventilation means for providing respiration to the patient comprising a third tube extending from the mouth far enough down the throat to provide a respiratory function to the patient,
    the improvement comprising:
    said elongated means being attached to said including stiffening means to enable said first tube to be placed down the throat of said patient without the use of a surgical instrument and said second and third tubes being attached to said elongated means to prevent said second and said third tubes from interfering with the surgery.

2. A laryngeal tube according to claim 1 wherein said stiffening means is a wire extending at least part way along the lengths of said second and said third tubes and connected to said second and said third tubes for an extended distance.

3. In a laryngeal tube as defined in claim 2, said wire being attached to said first tube and extending to the patient's mouth when the laryngeal tube is in use.

4. A laryngeal tube as defined in claim 3 having means for covering said wire to protect the patient from the wire.

5. A laryngeal tube as defined in claim 4 in which said last-named means is a sheath around the wire.

6. A laryngeal tube according to claim 5 wherein said wire is made of a flexible metal.

7. A laryngeal tube according to claim 5 wherein said wire is made of a soft iron.

8. A laryngeal tube according to claim 5 wherein said wire is made of copper.

9. A laryngeal tube according to claim 5 wherein said wire is made of aluminum.

10. A laryngeal tube as defined in claim 2 wherein said second and said third tubes and said wire are attached together outside of said first tube.

11. A laryngeal tube according to claim 5 wherein said wire is made of stainless steel.

12. A laryngeal tube according to claim 2 wherein said wire terminates within said first tube.

13. A laryngeal tube according to claim 2 wherein said wire and said third tube are attached together within said first tube and wherein said wire and said third tube are attached to the inside of said first tube.

14. A laryngeal tube according to claim 5 wherein said third tube and said sheath are attached together and define a wedge-shaped space between them, said second tube having a smaller diameter than said third tube, said second tube being located in the wedge-shape space between the sheath of said wire and said third tube.

15. A laryngeal tube according to claim 2 wherein said means for inflating the cuff is partially embedded within the wall of said first tube.

16. A laryngeal tube according to claim 2 wherein said first tube has a center line thereof and an elongated indent extending along the outer surface of said first tube parallel to the center line thereof, said second tube extending along said elongated indent to said inflatable means.

17. A laryngeal tube according to claim 16 wherein said first tube has rounded ends and further comprising a helical spring embedded within the wall of said first tube around the center line of said tube.

18. A laryngeal tube according to claim 17 wherein said helical spring is spaced inwardly from the ends of said first tube.

19. A laryngeal tube according to claim 2 wherein the second tube terminates near the midpoint of said first tube and wherein the third tube terminates at the first end of said first tube closest to the mouth of the patient.

20. A laryngeal tube according to claim 1 wherein the stiffening means is comprised of a plastics material.

21. A laryngeal tube according to claim 2 further comprising a pilot balloon attached to said second tube and a funnel attached to said third tube.

* * * * *